(12) United States Patent
Al-Masum (10) Patent No.: US 9,833,421 B2
(45) Date of Patent: Dec. 5, 2017

(54) METHOD FOR SYNTHESIZING (E)-ANETHOL AND RELATED COMPOUNDS BY CROSS COUPLING REACTION OF POTASSIUM ALLYLTRIFLUROBORATE AND 4-BROMOANISOLE AND ARYL HALIDES

(71) Applicant: Tennessee Board of Regents, Nashville, TN (US)

(72) Inventor: Mohammad Al-Masum, Nashville, TN (US)

(73) Assignee: Tennessee Board of Regents, Nashville, TN (US)

( * ) Notice: Subject to any disclaimer, the term of this patent is extended or adjusted under 35 U.S.C. 154(b) by 142 days.

(21) Appl. No.: 14/199,246

(22) Filed: Mar. 6, 2014

(65) Prior Publication Data
US 2014/0336270 A1  Nov. 13, 2014

Related U.S. Application Data

(63) Continuation of application No. 13/177,271, filed on Jul. 6, 2011, now abandoned.

(51) Int. Cl.
*A61K 31/085* (2006.01)
*C07C 1/00* (2006.01)
*C07B 37/04* (2006.01)
*C07C 1/32* (2006.01)
*C07C 41/30* (2006.01)

(52) U.S. Cl.
CPC ............ *A61K 31/085* (2013.01); *C07B 37/04* (2013.01); *C07C 1/00* (2013.01); *C07C 1/321* (2013.01); *C07C 41/30* (2013.01); *C07C 2523/44* (2013.01)

(58) Field of Classification Search
None
See application file for complete search history.

(56) References Cited

PUBLICATIONS

Yamamoto Y, Takada S, Miyaura N. γ-Selective Cross-Coupling of Potassium Allyltrifluoroborates with Aryl and 1-Alkenyl Bromides Catalyzed by a Pd (OAc) 2/D-t-BPF Complex. Chemistry Letter. 2006: 37(7); 704-705.

*Primary Examiner* — Dennis Heyer
(74) *Attorney, Agent, or Firm* — McBee Moore Woodard & Vanik IP, LLC; Susan McBee; Chester Moore (57) ABSTRACT

Methods of producing substituted and non-substituted beta-methyl styrene by a cross-coupling reaction are provided. The disclosure also provides for methods of preparing (E)-Anethol and related compounds by a cross coupling reaction of potassium allyltrifluoroborate and 4-bromoanisole and aryl halides. Compounds, compositions, and methods of treating disorders utilizing beta-methyl styrene are also provided.

11 Claims, 7 Drawing Sheets

Figure 1

(E)-Anethol

Figure 2

Scheme 1

Figure 3

Scheme 2

Method

Method A 1 to 2 (.25 mmol : .5 mmol)
PdCl$_2$(dppf)CH$_2$Cl$_2$ 5 mole %
K$_2$CO$_3$ 1.0 mmol
IPA/H$_2$O 2.5 mL
120 °C, 2 days

Method B 1 to 2 (.5 mmol : .5 mmol)
PdCl$_2$(dppf)CH$_2$Cl$_2$ 5 mole %
K$_2$CO$_3$ 1.0 mmol
IPA/H$_2$O 2.5 mL
MW, 120 °C, 20 min

Method C 1 to 2 (.625 mmol : .25 mmol)
PdCl$_2$(d$^t$bpf) 3 mole %
K$_2$CO$_3$ 1.0 mmol
IPA/H$_2$O 2.5 mL
MW, 120 °C, 20 min

Method C in conventional heating
for overnight

Observed by GC-MS

Figure 4

Figure 4:
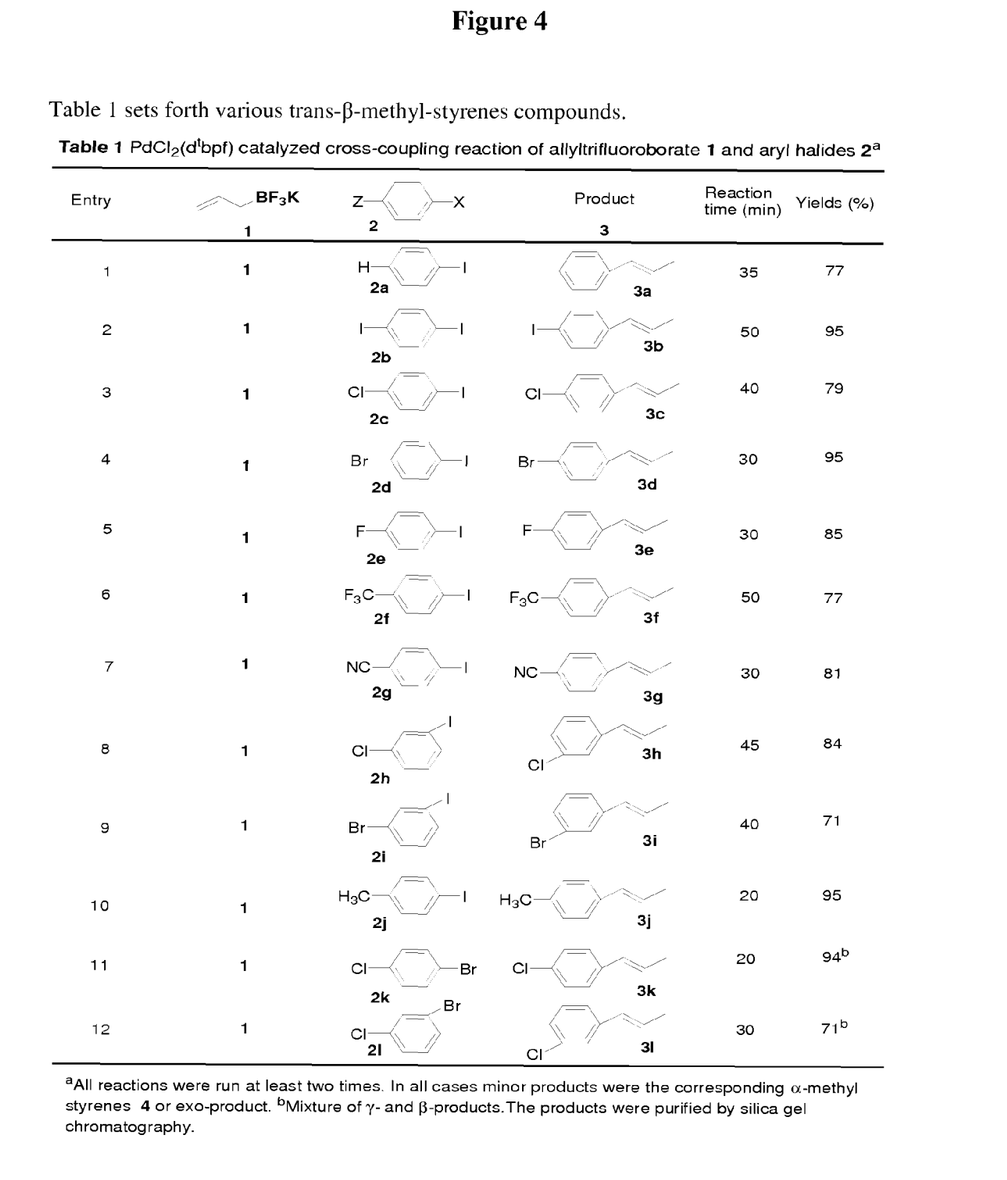
FIG. 4 provides for methods of producing various trans-β-methyl-styrenes products.

Table 1 sets forth various trans-β-methyl-styrenes compounds.

Table 1 PdCl$_2$(d$^t$bpf) catalyzed cross-coupling reaction of allyltrifluoroborate 1 and aryl halides 2[a]

| Entry | BF$_3$K (1) | Z—⟨⟩—X (2) | Product (3) | Reaction time (min) | Yields (%) |
|---|---|---|---|---|---|
| 1 | 1 | H—⟨⟩—I  2a | 3a | 35 | 77 |
| 2 | 1 | I—⟨⟩—I  2b | I—⟨⟩—  3b | 50 | 95 |
| 3 | 1 | Cl—⟨⟩—I  2c | Cl—⟨⟩—  3c | 40 | 79 |
| 4 | 1 | Br—⟨⟩—I  2d | Br—⟨⟩—  3d | 30 | 95 |
| 5 | 1 | F—⟨⟩—I  2e | F—⟨⟩—  3e | 30 | 85 |
| 6 | 1 | F$_3$C—⟨⟩—I  2f | F$_3$C—⟨⟩—  3f | 50 | 77 |
| 7 | 1 | NC—⟨⟩—I  2g | NC—⟨⟩—  3g | 30 | 81 |
| 8 | 1 | Cl—⟨⟩—I  2h | Cl—⟨⟩—  3h | 45 | 84 |
| 9 | 1 | Br—⟨⟩—I  2i | Br—⟨⟩—  3i | 40 | 71 |
| 10 | 1 | H$_3$C—⟨⟩—I  2j | H$_3$C—⟨⟩—  3j | 20 | 95 |
| 11 | 1 | Cl—⟨⟩—Br  2k | Cl—⟨⟩—  3k | 20 | 94[b] |
| 12 | 1 | Cl—⟨⟩—Br  2l | Cl—⟨⟩—  3l | 30 | 71[b] |

[a] All reactions were run at least two times. In all cases minor products were the corresponding α-methyl styrenes 4 or exo-product. [b] Mixture of γ- and β-products. The products were purified by silica gel chromatography.

Scheme 4

Z = Cl, 6a + 7a; Yield 54 %
Z = Br, 6b + 7b; Yield 41 %
Z = CH$_3$, 6c + 7c; Yield 77 %

Figure 7

| Compound from Table 1 | Analytical data for beta-methylstyrenes |
|---|---|
| 3a | 1H NMR (CDCl3, 300 MHz): d 7.30 (m, 4H, –C6H5), 6.42 (d, J = 15.9 Hz, 1H), 6.25 (dq, J = 15.9 Hz, 6.3 Hz, 1H) 1.89 (d, J = 6.3 Hz, 3H). LRMS: Calcd for C9H10 M+ 118. Found: 118 |
| 3b | 1H NMR (CDCl3, 300 MHz): d 7.48 (m, 4H, –4-I–C6H4), 6.32 (d, J = 15.9 Hz, 1H), 6.24 (m, 1H) 1.86 (d, J = 4.8 Hz, 3H). LRMS: Calcd for C9H9I M+ 244. Found:244 |
| 3c | 1H NMR (CDCl3, 300 MHz): d 7.24 (m, 4H, –4-Cl–C6H4), 6.27 (d, J = 15.3 Hz, 1H), 6.14 (dq, J = 15.3 Hz, 6.3 Hz, 1H) 1.81 (d, J = 6.3 Hz, 3H). LRMS: Calcd for C9H9Cl (M+2)+ 154. Found: 154 |
| 3e | 1H NMR (CDCl3, 300 MHz): d 7.20 (m, 4H, –4-F–C6H4), 6.37 (d, J = 15.6 Hz, 1H), 6.15 (dq, J = 16.2 Hz, 6.9 Hz, 1H) 1.87 (d, J = 6.3 Hz, 3H). LRMS: Calcd for C9H9F M+ 136.Found: 136 |
| 3f | 1H NMR (CDCl3, 300 MHz): d 7.42 (m, 4H, –4-CF3–C6H4), 6.44 (d, J = 15.9 Hz, 1H), 6.36 (m, 1H) 1.93 (d, J = 5.4 Hz, 3H). 19F NMR (CDCl3, 282.3 MHz): d _62.786. LRMS: Calcd for C10H9F3 M+ 186. Found: 186 |
| 3g | 1H NMR (CDCl3, 300 MHz): d 7.36 (m, 4H, –4-CN–C6H4), 6.3 (m, 1H), 6.32 (m, 1H) 1.85(d, J = 3.6 Hz, 3H. Calcd for C10H9N M+ 143. Found: 143 |
| 3h | 1H NMR (CDCl3, 300 MHz): d 7.24 (m, 4H, –3-Cl–C6H4), 6.35 (d, J = 16.8 Hz, 1H), 6.25 (m, 1H) 1.89 (d, J = 5.4 Hz, 3H). Calcd for C9H9Cl M+ 152. Found: 152 |
| 3i | 1H NMR (CDCl3, 300 MHz): d 7.37 (m, 4H, –3-Br–C6H4), 6.33(d, J = 15.9 Hz, 1H), 6.24 (dq, J = 15.9 Hz, 6.0 Hz, 1H), 1.89 (d, J = 5.1 Hz, 3H). Calcd for C9H9Br M+ 198. Found: 198 |
| 3j | 1H NMR (CDCl3, 300 MHz): d 7.10 (m, 4H, –4-Me–C6H4), 6.29 (d, J = 5.6 Hz, 1H), 6.10 (dq, J = 14.1 Hz, 6.6 Hz, 1H) 1.81 (d, J = 6.6 Hz, 3H). Calcd for C10H12 M+ 132. Found: 132 |
| 3k | 1H NMR (CDCl3, 300 MHz): d 7.20 (m, 4H, –4-Cl–C6H4), 6.31 (d, J = 15.9 Hz, 1H), 5.84 (m, 1H) 1.81 (d, J = 6.3 Hz, 3H). Calcd for C9H9Cl M+ 152. Found: 152 |
| 3l | 3l 1H NMR (CDCl3, 300 MHz): d 7.26 (m, 4H, –3-Cl–C6H4), 6.35 (d, J = 17.0 Hz, 1H), 6.29 (m, 1H) 1.81 (d, J = 6.3 Hz, 3H). Calcd for C9H9Cl M+ 152. Found: 152. |

METHOD FOR SYNTHESIZING (E)-ANETHOL AND RELATED COMPOUNDS BY CROSS COUPLING REACTION OF POTASSIUM ALLYLTRIFLUROBORATE AND 4-BROMOANISOLE AND ARYL HALIDES

CROSS REFERENCE TO RELATED APPLICATIONS

This application is a continuation of U.S. patent application Ser. No. 13/177,271, filed Jul. 6, 2011, which claims priority to U.S. Provisional Appl. No. 61/399,054, filed Jul. 6, 2010, the content of which both of these application is herein incorporated by reference in their entirety.

FIELD

The disclosure relates to methods of preparing substituted and non-substituted beta-methyl styrene compounds by a cross-coupling reaction. In an aspect, the disclosure relates to a method of preparing (E)-Anethol by a cross coupling reaction of potassium allyltrifluoroborate and 4-bromoanisole.

BACKGROUND (E)-Anethol is a useful organic compound for whose fragrance is widely used in the fragrance industry for perfumes, scented candles, and numerous related products. It is also widely used in the production of alcoholic beverages such as raki, uzo, pernod, anisette, ricard, and granier where an aromatic fragrance is a part of the beverage's character. In certain countries, (E)-Anethol is used in the food and pharmaceutical industries and recently been investigated as an insect repellant as well.

Naturally occurring sources of Anethol isomers are found in the varieties of the anise, camphor, and fennel plants. (E)-Anethol is derived from these plants by a process of crushing and water distillation. The resulting amount of (E)-Anethol obtained from this process is quite low—with a 3.5% (E)-Anethol yield considered to be very good. The demand for the compound, coupled with the inefficient process used to obtain it, has caused others to try and produce a synthetic version of (E)-Anethol. Until now, those efforts have been unsuccessful. In an aspect, the disclosure provides for a novel, non-obvious and useful method for synthetically producing beta-methyl styrene compounds. In another aspect, the disclosure provides for a novel, non-obvious and useful method for synthetically producing (E)-Anethol and related compounds.

Similarly, potassium organotrifluoroborates have been shown to be an indispensable class of transformative organic reagents for wide range of cross-coupling reactions. The possible combinations of electrophiles and nucleophiles in cross-coupling reactions of allylic metals with aryl, alkenyl, and allyl electrophiles, or their reversed combination, are important due to the frequent occurrence of these fragments in natural products. In light of their low toxicity and operational simplicity, attempts have been made to use potassium allyltrifluoroborates as allylating agents. However, until now success in such efforts has been largely unknown. In another embodiment of the disclosure (E)-Anethol is synthesized from a palladium catalyst system utilizing microwave-enhanced coupling of potassium allyltrifluoroborates and aryl halides.

Transition metal catalyzed cross-coupling reaction method is extensively applied in modern chemistry for carbon-carbon bond formation reaction. Following the recent application of potassium organotrifluoroborates in organic transformations, further advances of this field especially with microwave irradiation in water have recently been made. The instant description focuses on the development of a new catalyst system for allylation reactions that involve potassium allyltrifluoroborates, organic halides as electrophiles, water as a solvent, and microwave activation.

SUMMARY

In an aspect the disclosure provides for a method of producing a styrene compound by a reaction comprising, consisting of, or consisting essentially of reacting a potassium trifluoroborate with an aryl halide compound of Formula (I)

Formula (I)

wherein

X is selected from the group consisting of I, Br, OTf, ONf, ODs, and OAc; and

Z is selected from the group consisting of F, Cl, Br, I, CN, —$SO_3H$, —$CO_2H$, —CHO, —$NO_2$, $CF_3$, $CCl_3$, and an alkyl group. In an aspect, the reaction is catalyzed by a palladium salt. In another aspect, the palladium salt can be selected from the group consisting of Pd(OAc)$_2$, PdCl$_2$(dppf) CH$_2$Cl$_2$, PdCl$_2$ (d$^t$bpf), Pd$_2$(dba)CHCl$_3$ PdCl$_2$ (dphos)$_2$, Pd(dba)$_2$, PdCl$_2$ (dtbpf), and Pd(Ph$_3$)$_2$.

The disclosure also provides for a method of producing an Anethol compound, for example, (E)-Anethol, by a method comprising, consisting of, or consisting essentially of reacting a potassium allyltrifluoroborate with 4-bromoanisole. In another aspect, the methods disclosed herein are catalyzed with a palladium salt, for example, Pd(OAc)$_2$, PdCl$_2$(dppf) CH$_2$Cl$_2$, PdCl$_2$ (d$^t$bpf), Pd$_2$(dba)CHCl$_3$ PdCl$_2$ (dphos)$_2$, Pd(dba)$_2$, PdCl$_2$ (dtbpf), or Pd(Ph$_3$)$_2$. In another aspect, the methods described herein further comprise heating potassium allyltrifluoroborate and said 4-bromoanisole from about 100° C.-150° C. for about 10 to about 60 minutes. In yet another aspect, the methods described herein can include potassium allyltrifluoroborate and said 4-bromoanisole are present in a ratio of about 4:1 to about 1:1 or a ratio of about 4:1.

The disclosure also provides for a method of administering a compound described herein, for example, (E)-Anethol, to a patient in need thereof to treat a disorder selected from the group consisting of a viral infection, HIV, Hepatitis C, herpes simplex virus-1, herpes simplex virus-2, vesicular stomatitis virus, parainfluenza-3 coxsackie B3, and sindbid virus.

BRIEF DESCRIPTION OF THE DRAWINGS

FIG. 7 provides for analytical data of beta-methylstyrenes of Table 1.

DETAILED DESCRIPTION SUMMARY

In an aspect, the disclosure provides for a method of producing substituted and non-substituted beta-methyl styrene compounds by the methods disclosed herein. In another aspect, as an example, the disclosure provides for the following reaction:

Scheme A

In an aspect, "Z" may be an electron withdrawing or an electron donating group. In another aspect, "Z" may be a halogen group. In an aspect, "Z" may be an F, Cl, Br, or I. In yet another aspect, "Z" may be independently selected from a cyano group, such as CN, a sulfonate group, such as —$SO_3H$, —$CO_2H$, an ester group, such as —$CO_2R$, an aldehyde group, such as —CHO, a ketone group, such as —COR, a nitro group, such as —$NO_2$, a quaternary amine/quaternary ammonium base, such as $NR_3^+$, a trihalide group, such as —$CF_3$ or $CCl_3$, or an alkyl group. In another aspect, "Z" may be independently selected from methyl, ethyl, propyl, isopropyl, cyclopropyl, butyl, tert-butyl, pentyl, tert-butyl, pentyl, hexyl, heptyl, octyl, nonyl, decyl, substituted or non substituted $C_2$-$C_{12}$-alkyl, substituted or non substituted $C_2$-$C_{12}$-alkenyl, substituted or non substituted $C_2$-$C_{12}$-alkynyl, or a $(CH_2)_3$ ring structure, $(CH_2)_4$ ring structure, $(CH_2)_5$ ring structure, $(CH_2)_6$ ring structure, $(CH_2)_7$ ring structure, or $(CH_2)_8$ ring structure. In an aspect, "R" is selected from the group consisting of methyl, ethyl, propyl, isopropyl, cyclopropyl, butyl, tert-butyl, pentyl, tert-butyl, pentyl, hexyl, heptyl, octyl, nonyl, decyl, and a substituted or non substituted $C_2$-$C_{12}$-alkyl.

In an aspect, "X" may be a may be a halogen group or may be selected from I, Br, OTf, ONf, ODs, or OAc. In another aspect, "X" is not Cl or F. In an aspect, compound "1" is a potassium trifluoroborate, such as potassium allyltrifluoroborate. In another aspect, compound "1" is an alkyl substituted boronic acid compound.

In another aspect, the disclosure provides for a method of producing (E)-anethol by the following Scheme B:

Scheme B 3
(E)-Anethol

In an aspect, potassium allyltrifluoroborate and 4-bromoanisole are in a ratio of 4:1 in Scheme B.

In an aspect, a beta-methyl styrene is synthesized by a palladium-catalyzed cross-coupling reaction of potassium allyltrifluoroborate and 4-bromoanisole in water/isopropanol under heating. In another aspect, (E)-anethol is synthesized by a palladium-catalyzed cross-coupling reaction of potassium allyltrifluoroborate and 4-bromoanisole in water/isopropanol under microwave heating. A significant advantage of using potassium allyltrifluoroborate is that it is stable and can be readily prepared compared to the corresponding allylboronic esters. In an aspect, the reaction is completed within 30 min with a high yield of (E)-Anethol regioselectively.

In an aspect, methods disclosed herein result in an increased yield of substituted and non-substituted beta-methyl styrene compounds. In another aspect, methods disclosed herein result in an increased yield of (E)-Anethol or any one of compounds 3a-3l as set forth in Table 1. In an aspect, the improved yield is relative to conventional methods. In another aspect, the improved yield is relative to traditional methods of purifying (E)-Anethol, for example, in methods involving crushing plants and water distillation. In yet another aspect, the yield of the product, for example, substituted and non-substituted beta-methyl styrene compounds, (E)-Anethol, or any one of compounds 3a-3l as set forth in Table 1, may be from about 5%-99.9%, from about 10%-99%, from about 20%-90%, from about 30%-80%, from about 50%-99%, from about 60%-99%, from about 70%-99%, from about 70%-95%, from about 80%-99%, from about 90%-99%, greater than 50%, greater than 60%, greater than 70%, greater than 80%, greater than 85%, greater than 90%, greater than 95%, greater than 95%, about 75%, about 90%, about 95%, about 96%, about 97%, about 98%, or about 99%.

In an aspect, the ratio of compound "1" to compound "2" present in the reaction is from about 10:1 to about 1:10, 8:1 to about 1:8, from about 5:1 to about 1:5, from about 4:1 to about 1:4, from about 3:1 to about 1:3, from about 5:1 to about 3:1, from about 5:1 to about 2:1, from about 4:1 to about 3:1, from about 4:1 to about 2:1, from about 4:1 to about 1:1, about 1:1, about 2:1, about 3:1, about 4:1, about 5:1, about 6:1, or about 10:1. In another aspect, the disclosure provides for a ratio of compound "1" to compound "2" of from about 5:1 to about 3:1, from about 5:1 to about 2:1, from about 4:1 to about 3:1, from about 4:1 to about 2:1, from about 4:1 to about 1:1, about 1:1, about 2:1, about 3:1, or about 4:1 results in a product yield of between about 5%-99.9%, about 10%-99%, about 20%-90%, about 30%-80%, about 50%-99%, about 60%-99%, about 70%-99%, about 70%-95%, about 80%-99%, about 90%-99%, greater than 50%, greater than 60%, greater than 70%, greater than 80%, greater than 85%, greater than 90%, greater than 95%, greater than 95%, about 75%, about 90%, about 95%, about 96%, about 97%, about 98%, or about 99%.

In another aspect, the methods disclosed herein may employ microwave or other conventional heating sources. In an aspect, the methods disclosed herein may employ heating from about 50° C.-250° C., from about 80° C.-200° C., from about 100° C.-180° C., from about 100° C.-150° C., from about 100° C.-140° C., from about 100° C.-130° C., from about 110° C.-130° C., about 100° C., about 110° C., about 120° C., about 130° C., about 140° C., about 150° C. In another aspect, the methods disclosed herein may employ any of the above temperatures for a time period of from about 10 minutes to about 4 hours, from about 10 minutes to about 2 hours, from about 10 minutes to about 60 minutes, and from about 20 minutes to about 40 minutes. In yet another aspect, the methods disclosed herein may employ microwave or conventional heating from about 10 minutes to about 4 hours, from about 10 minutes to about 2 hours, from about 10 minutes to about 60 minutes, and from about 20 minutes to about 40 minutes.

Figure 2:
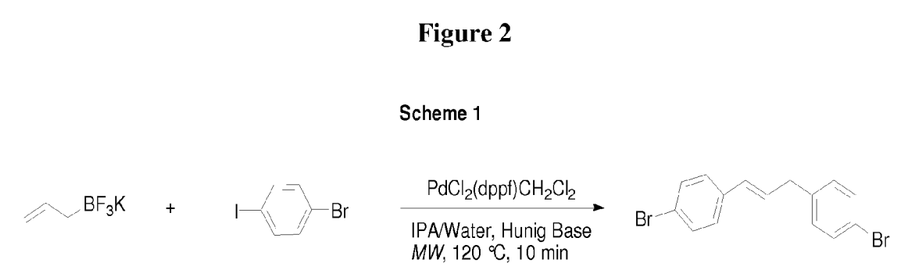
FIG. 2 provides for a method of obtaining a product by the reaction of potassium allyltrifluoroborate with 4-bromoiodobenzene in the presence of a palladium catalyst in isopropanol/water.

In an aspect, potassium allyltrifluoroborate is treated with 4-bromoiodobenzene in the presence of a palladium catalyst in isopropanol/water (IPA/water) under microwave irradiation. Under such a condition, for example, a coupling product as set forth in FIG. 2/Scheme 1 was obtained. In another aspect, to obtain an efficient catalyst for homoallylation reactions using potassium allyltrifluoroborates and aryl halides, various palladium salts such as Pd(OAc)2, PdCl2(dppf)CH2Cl2, Pd2(dba)3CHCl3, PdCl2(dphos)2, Pd(dba)2, PdCl2(dtbpf), and Pd(Ph3P)4 and ligands such as dppb, dppf, Ph3P, and dppe were introduced.

Figure 3:
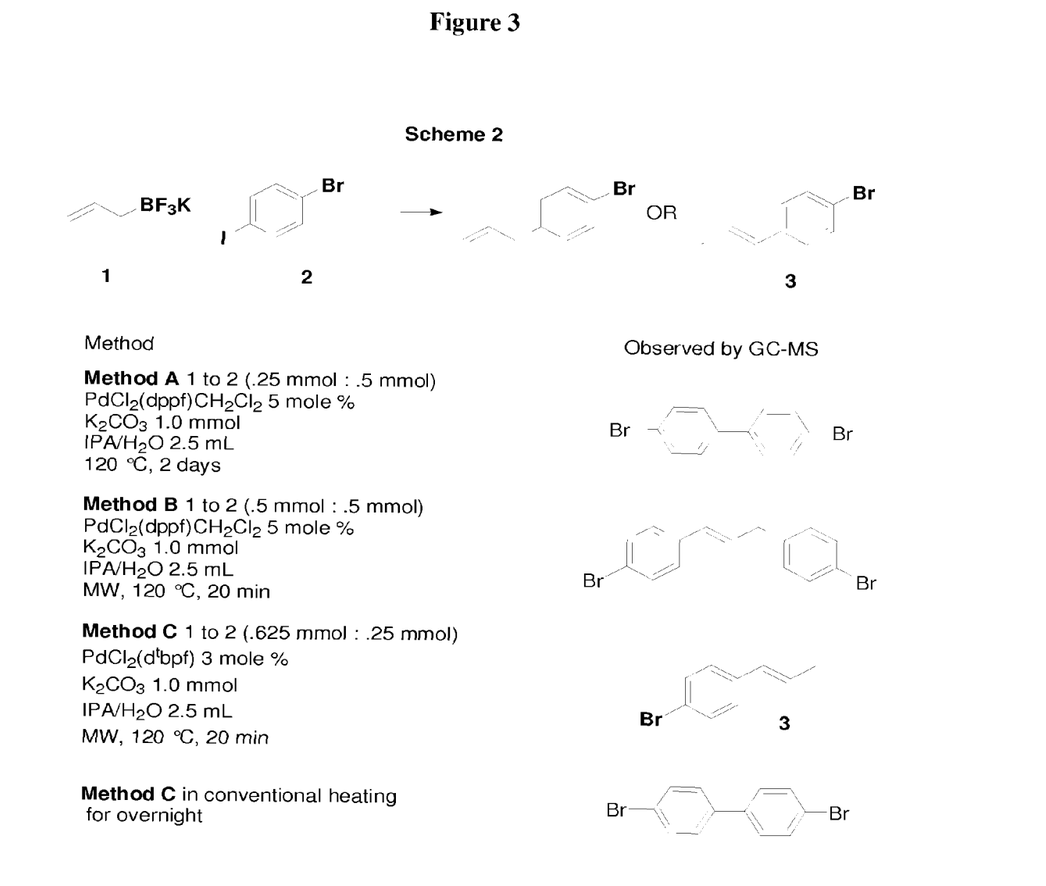
FIG. 3 provides for methods of obtaining a product by utilizing different ratios of a palladium catalyst under varied experimental conditions.

In another aspect, a base may be used with the methods disclosed herein. In an aspect, the base may be KF, Cs2CO3, K2CO3, KOH, and iPr2NEt; solvents such as water, IPA/water, and THF/water. FIG. 3 (Scheme 2) details different reaction conditions obtained by using both microwave heating and conventional heating.

In another aspect, the disclosure provides for a method of utilizing anethol, (E)-anethol, or any one of compounds 3a-3l as set forth in Table 1 either alone, or in combination with other chemical compounds, in a method for treating cancer or cancerous tumors. In another aspect, the disclosure provides for a method of utilizing anethol, (E)-anethol, or any one of compounds 3a-3l as set forth in Table 1 either alone, or in combination with other chemical compounds, in a method for treating viral infections, including but not limited to HIV, Hepatitis C and herpes simplex virus-1, herpes simplex virus-2, vesicular stomatitis virus, parainfluenza-3 coxsackie B3, and sindbid virus. In another aspect, compounds disclosed herein, either alone or in combination with appropriate cancer treating compositions or compounds, may be employed in a method for treating cancer or cancerous tumors wherein the compounds are injected into the body of the person being treated at or near the location of the tumor, introduced into the body orally or in the form of a liquid, or are introduced into the body orally in the form of a solid capsule. In another aspect, any of the compounds described herein may be injected into the body of the person being treated at or near the location of a tumor, introduced into the body orally or in the form of a liquid, or are introduced into the body orally in the form of a solid capsule.

The disclosure also provides for methods of producing the disclosed compounds comprising, consisting of, or consisting essentially of utilizing any of the methodology disclosed herein. In another aspect, the disclosure provides for methods of producing anethol, (E)-anethol, or any one of compounds 3a-3l as set forth in Table 1 comprising, consisting of, or consisting essentially of utilizing the methods set forth in, for example, Scheme A, or any of the methods disclosed herein. The disclosure additionally provides for compositions comprising, consisting of, and consisting essentially of any of the disclosed compounds, for example, anethol, (E)-anethol, or any one of compounds 3a-3l as set forth in Table 1 as produced by the disclosed methods.

EXAMPLES

Example 1

Figure 1:
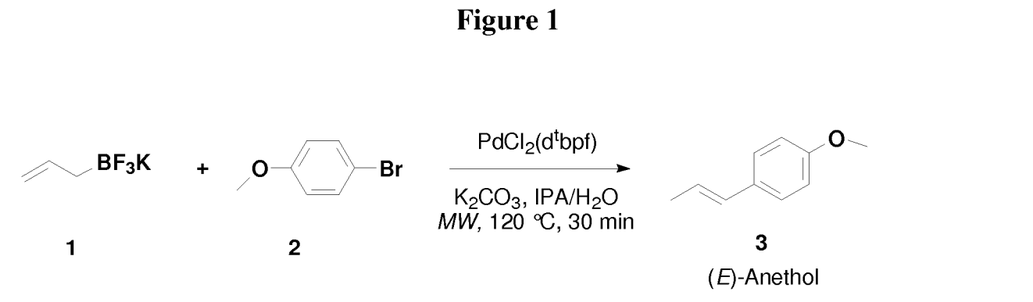
FIG. 1 provides for a method of preparing (E)-Anethol.

In this example, (E)-Anethol is prepared by the following procedure: Potassium allyltrifluoroborate (148.0 mg, 1.0 mmol), 4-bromoianisole (32 L, 0.25 mmol), (a 4:1 ratio of potassium allyltrifluoroborate and 4-bromoanisole respectively), $K_2CO_3$ (104.0 mg, 0.75 mmol) and $PdCl_2(d^tbpf)$ (5.0 mg, 0.0075 mmol, 3 mol %) were placed in an argon flushed pyrex tube. The pyrex tube was capped with a rubber septum, flushed with argon and 2.5 mL of isopropanol/water (2:1) was added. The resulting mixture in the pyrex tube was placed in a CEM microwave unit and allowed to irradiate at 120° C. for 30 minutes. As an example, preparation of (E)-Anethol by this method is set forth in FIG. 1.

After standard work-up by adding ammonium chloride and ethyl ether, the ether layer was separated. The reaction mixture was adsorbed in a silica gel plate for preparative TLC with hexane as the eluent and the developed TLC plate was exposed to a UV lamp and the intense spot for the product was marked. The collected compound adsorbed in the silica gel was washed with ethyl ether, filtered, dried the filtrate to get the desired product. The pure product (E)-Anethol was isolated in 97% yield. In another aspect, the preparative TLC the product can also be purified by subjected to silica gel chromatography using hexane as an eluent.

Example 2

In this example, Potassium allyltrifluoroborate 1 (93.0 mg, 0.625 mmol), 4-bromoiodobenzene 2d (71.0 mg, 0.25 mmol), K2CO3 (104.0 mg, 0.75 mmol), and PdCl2(dtbpf) (0.0075 mmol, 3 mol %) were placed in an argon-flushed pyrex tube. The pyrex tube was capped with a rubber septum, flushed with argon, and 2.5 mL of isopropanol/water (2:1) was added.

The resulting mixture present in the pyrex tube was placed in a CEM microwave unit and allowed to irradiate at 120 C for 30 min. After adding ammonium chloride and ethyl ether, the ether layer was separated. The reaction mixture was adsorbed in silica gel and transferred into the column and was subjected to silica gel chromatography using hexane as an eluent. The pure product 4-bromo-trans-b-methylstyrene, compound 3d (from Table 1) was isolated in a 95% yield (FIG. 4, Table 1, Entry 4) 1H NMR (CDCl3, 300 MHz): d 7.22 (m, 4H, -4-Br—C6H4), 6.26 (d, J=16.8 Hz, 1H), 6.24 (dq, J=15.8 Hz, 6.3 Hz, 1H) 1.80 (d, J=5.7 Hz, 3H). LRMS Calculated for C9H9Br M+197. Found: 197.

Example 3

In this example, in method A (see FIG. 3), a 1 to 2 ratio of potassium allyltrifluoroborate 1 and 4-bromoiodobenzene (compound 2d from Table 1) along with 5 mol % of PdCl2(dppf)CH2Cl2 and 4 equiv of K2CO3 were added in 1 M solution of isopropanol-water and refluxed for overnight. The reaction progress was monitored by GC-MS. No allylation was observed but the homo-coupling product 4,40-dibromo biphenyl, along with starting dihalo compounds, was observed.

Example 4

In this example, in method B, (see FIG. 3) changing the proportion of potassium allyltrifluoroborate 1 and 4-bromoiodobenzene (compound 2d from Table 1) to 1:1 along with the same loading of catalyst and base as set forth in Example 3 in isopropanol-water and the reaction mixture irradiated under microwave heating system generated the allylated product along with the double addition product shown previously in Scheme 1. The reproducibility of this reaction was not reliable.

Example 5

In this example, switching to a new palladium salt PdCl2 (dtbpf) in method C (see FIG. 3) led to a new catalyst system that performed in a selective monoallylation fashion. The combination of a PdCl2(dtbpf) catalyst, 4-bromoiodobenzene, K2CO3, and water-isopropanol under microwave irradiation for 30 min produced allyl coupling products with remarkable regioselectivity (FIG. 3, Scheme 2). The potassium allyltrifluoroborate was prepared using the known method (See, for example, Vedejs, et al. J. Org. Chem. 1995, 60, 3024 and Batey et al. Tetrahedron Lett. 1999, 40, 4289, the contents of which are hereby incorporated by reference in their entirety) and was then treated with various dihalides such as 1,4-diiodobenzene (compound 2b from Table 1), 4-chloroiodobenzene (compound 2c from Table 1), 4-bromoiodobenzene (compound 2d from Table 1), and 4-fluoroiodobenzene (compound 2e from Table 1) applying method C. In each of the above cases, allylation reactions took place at the central carbon, b-carbon selectivity. When iodobenzene (compound 2a from Table 1) was employed the same selectivity was observed. When the catalyst was used in excess the starting material disappeared rapidly but the homocoupled product predominated.

Example 6

In this example, the influence of substituents on aromatic rings, functional groups attached to the aryl rings, such as CF3, CN, and CH3, were introduced by following the reaction conditions described in method C of Scheme 2. Reactions furnished successful cross-coupling allylation compounds, 3f, 3g, and 3j with beta-carbon selectivity (FIG. 4, Table 1, Entries 6, 7, and 10). 3-Chloroiodobenzene (compound 2h from Table 1) and 3-bromoiodobenzene (compound 2i from Table 1), also gave the corresponding trans-b-methylstyrenes (compounds 3h and 3i, respectively, from Table 1) (FIG. 4, Table 1, Entries 8 and 9).

The ratio of the central carbon selectivity with endo-products ArCH@CHCH3 (compounds 3a-3j from Table 1), and exo-products ArC(CH3)@CH2 4a-4-j was 5:1. In case of 4-methyliodobenzene, (compound 2j from Table 1), the ratio was 3:2 (FIG. 4, Table 1, Entry 10). The endo- and exo-products were unable to be separated by chromatography. For simplification, exo-products were not shown.

Example 7

Figure 5:
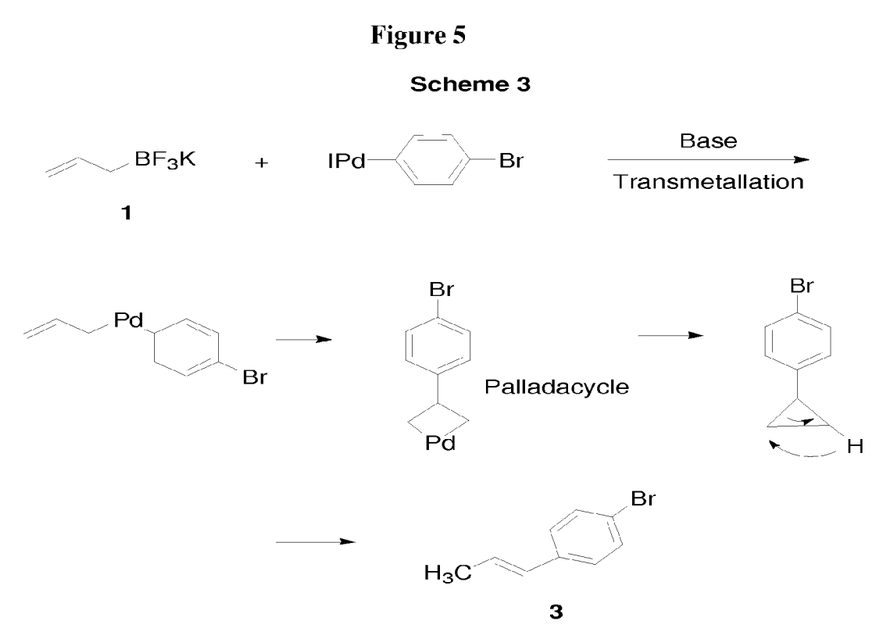
FIG. 5 provides for an example mechanism for cyclopropanation.
Figure 6:
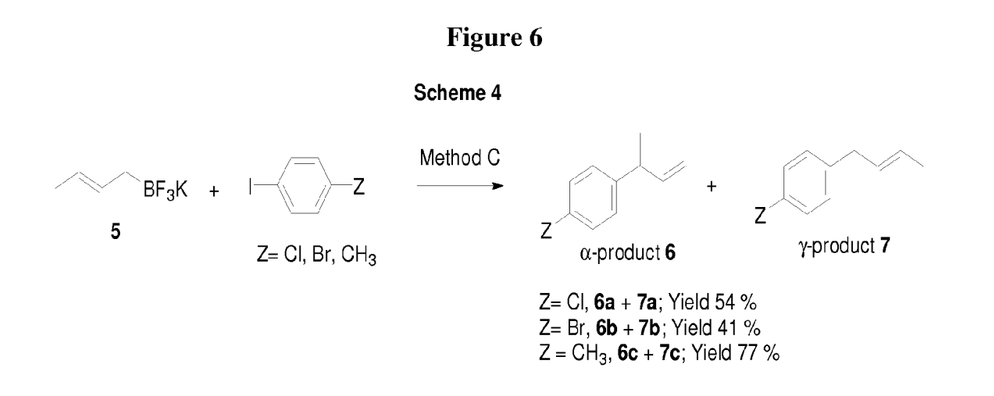
FIG. 6 provides for an example of a coupling product.

In this example, 4-chlorobromobenzene, (compound 2k from Table 1) and 3-chlorobromobenzene (compound 2l from Table 1), also underwent the coupling reaction but selectivity was poor. C— or terminal carbon addition products predominated along with b- or central carbon addition products (FIG. 4, Table 1, Entries 11 and 12). The ratio was c:b (3:2). It was noted that GC-MS analysis showed complete conversion to the product but when the reaction mixture was subjected to silica gel chromatography, some of the products were lost. Product volatility could be the cause of the loss. The highlighted part of this new transformation is regioselectivity. The generally accepted mechanism for this type of reaction involves nucleophilic attack on a cationic p-allylpalladium complex at the terminal or c-carbon, in some cases at the a-carbon. Louis Hegedus's pioneering report on the carbanion attacking the central carbon of the p-allyl complex greatly supports the present observation. A reasonable mechanism for cyclopropanation involves direct nucleophilic attack on the central carbon of the p-allyl system to form palladacyclobutane, followed by reductive elimination to produce the cyclopropane which presumably isomerizes to trans-b-methylstyrene (FIG. 5, Scheme 3). Interestingly, when same reaction condition (method C) was applied to potassium crotyltrifluoroborates and aryl halides, coupling products with a-selectivity were predominated along with trace amount of c-adduct (FIG. 6, Scheme 4). Analytical data for beta-methylstyrenes of Table 1 is set forth in FIG. 7.

The invention claimed is:

1. A method of synthetically producing (E)-Anethol comprising reacting a potassium allyltrifluoroborate with 4-bromoanisole, wherein the reaction produces a yield of (E)-Anethol from about 80%-99%.

2. The method of claim 1, wherein the reaction produces a yield of (E)-Anethol from about 90%-99%.

3. A method of synthetically producing (E)-Anethol comprising reacting a potassium allyltrifluoroborate with 4-bromoanisole, wherein the reaction produces a yield of (E)-Anethol of 5% or greater, wherein the reaction is catalyzed by a palladium salt, wherein said palladium salt is $PdCl_2$ ($d^tbpf$).

4. A method of synthetically producing (E)-Anethol comprising reacting a potassium allyltrifluoroborate with 4-bromoanisole, wherein the reaction further comprises heating said potassium allyltrifluoroborate and said 4-bromoanisole from about 100° C.-150° C. for about 10 to about 60 minutes.

5. The method of claim 4, wherein the reaction is catalyzed by a palladium salt.

6. The method of claim 5, wherein said palladium salt is selected from the group consisting of Pd(OAc)2, $PdCl_2$ (dppf)CH$_2$Cl$_2$, $PdCl_2$ ($d^tbpf$), $Pd_2$(dba)CHCl$_3$ $PdCl_2$ (dphos)$_2$, Pd(dba)$_2$, $PdCl_2$ (dtbpf), and Pd(Ph$_3$)$_2$.

7. The method of claim 4, wherein said potassium allyltrifluoroborate and said 4-bromoanisole are present in a ratio of about 5:1 to about 1:5.

8. The method of claim 4, wherein said potassium allyltrifluoroborate and said 4-bromoanisole are present in a ratio of about 4:1 to about 1:2.

9. The method of claim 4, wherein said potassium allyltrifluoroborate and said 4-bromoanisole are present in a ratio of about 4:1 to about 1:1.

10. The method of claim 4, wherein said potassium allyltrifluoroborate and said 4-bromoanisole are present in a ratio of about 4:1.

11. The method of claim 10, wherein the reaction is catalyzed by a palladium salt.

* * * * *